United States Patent [19]

Felix et al.

[11] Patent Number: 4,629,499
[45] Date of Patent: Dec. 16, 1986

[54] HERBICIDE COMPOSITIONS OF EXTENDED SOIL LIFE

[75] Inventors: Raymond A. Felix, Richmond; Joanna K. Hsu, Sunnyvale, both of Calif.

[73] Assignee: Stauffer Chemical Company, Westport, Conn.

[21] Appl. No.: 589,830

[22] Filed: Mar. 15, 1984

Related U.S. Application Data

[63] Continuation of Ser. No. 398,059, Jul. 14, 1982, abandoned.

[51] Int. Cl.$^4$ ............................................. A01N 25/22
[52] U.S. Cl. ........................................ 71/100; 71/101
[58] Field of Search ................................. 71/100, 101

[56] References Cited

U.S. PATENT DOCUMENTS

| | | | |
|---|---|---|---|
| 2,791,605 | 5/1957 | Dorman et al. | 71/101 |
| 3,131,509 | 5/1964 | Hoffmann | 71/77 |
| 3,133,810 | 5/1964 | Hamm | 71/101 |
| 3,607,870 | 9/1971 | Becke et al. | 260/501.12 |
| 4,003,735 | 1/1977 | Czajkowski et al. | 71/100 |
| 4,299,616 | 11/1981 | Hyzak | 71/106 |

FOREIGN PATENT DOCUMENTS 219675 2/1958 Australia .
0092204 7/1981 Japan .

OTHER PUBLICATIONS

PPG, Tech. Serv. Bull. 105-F-1 (1970) pp. 1-11.

Primary Examiner—Catherine L. Mills
Attorney, Agent, or Firm—Paul R. Martin

[57] ABSTRACT

Herbicidally active thiolcarbamates are employed in combination with certain allyl amine salts of thiocarbamic acid compounds having the formula

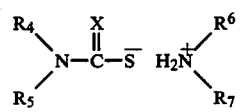

wherein $R_4$ and $R_5$ are independently selected from the group consisting of allyl, alkyl substituted allyl, and lower alkyl groups having from about 1 to about 6 carbon atoms;

$R_6$ and $R_7$ are independently selected from the group consisting of allyl, alkyl substituted allyl, and lower alkyl groups having from about 1 to about 6 carbon atoms; and X is oxygen or sulfur wherein at least one of $R_4$ and $R_5$ and at least one of $R_6$ and $R_7$ is an allyl group. In a typical application, the allyl amine salt of thiocarbamic acid compound is included in sufficient quantity to lessen the rate of soil degradation of the thiolcarbamate. As a result, the herbicidal effectiveness of the thiolcarbamate is enhanced and prolonged, rendering single application of the herbicide effective over a longer period of time.

9 Claims, No Drawings

HERBICIDE COMPOSITIONS OF EXTENDED SOIL LIFE

This is a continuation of application Ser. No. 398,059, filed July 14, 1982, abandoned.

BACKGROUND OF THE INVENTION

This invention relates to herbicidal compositions and methods of use. In particular, this invention relates to herbicidal compositions comprising an herbicidally active thiolcarbamate in combination with certain allyl amine salts of thiocarbamic acid compounds, the latter serving to prolong the effectiveness of a single application of the thiolcarbamate in controlling undesired plant growth.

Thiolcarbamates are well known in the agricultural art as herbicides useful for weed control in crops such as corn, potatoes, beans, beets, spinach, tobacco, tomatoes, alfalfa, rice and others. Thiolcarbamates are primarily used in pre-emergence application, and are particularly effective when incorporated into the soil prior to the planting of the crop. The concentration of the thiolcarbamate in the soil is greatest immediately after application of the compound. How long thereafter the initial concentration is retained depends in large part on the particular soil used. The rate at which the thiolcarbamate concentration declines following its application varies from one type of soil to the next. This is evident both in the observable extent of weed control and in the detectable presence in undegraded thiolcarbamate remaining in the soil after considerable time has elapsed.

It is therefore an object of this invention to increase the soil persistence of thiolcarbamate herbicides and thus improve their herbicidal effectiveness.

BRIEF DESCRIPTION OF THE INVENTION

It has now been discovered that the soil persistence of certain herbicidally active thiolcarbamates is significantly extended by the further addition to the soil of certain extender compounds in the form of certain allyl amine salts of thiocarbamic acid compounds, which have little or no herbicidal activity of their own and do not decrease the herbicidal activity of the thiolcarbamate. This improvement in the soil persistence of thiolcarbamates manifests itself in a variety of ways. It can be shown, for example, by soil analyses taken at regular intervals, that the rate of decrease of the thiolcarbamate content of the soil is substantially lessened. Improved soil persistence can also be shown by improvements in herbicidal efficacy, as evidenced by a higher degree of weed injury brought about when the extender compound increases the soil persistence of the thiolcarbamate, prolonging its effective life.

In particular, this invention relates to a novel herbicidal composition comprising (a) an herbicidally effective amount of a thiolcarbamate having the formula $$R^1-S-\overset{O}{\overset{\|}{C}}-N\overset{R^2}{\underset{R^3}{\diagdown}}$$

in which $R^1$, $R^2$, and $R^3$ are independently $C_1$–$C_6$ alkyl; and (b) an amount of a allylamine salt of thiocarbamic acid compound sufficient to extend the soil life of said thiolcarbamate, said salt compound having the formula, in salt form $$\overset{R_4}{\underset{R_5}{\diagdown}}N-\overset{X}{\overset{\|}{C}}-S^-\ H_2\overset{+}{N}\overset{R^6}{\underset{R_7}{\diagup}}$$

wherein $R_4$ and $R_5$ are independently selected from the group consisting of allyl, alkyl substituted allyl, and lower alkyl groups having from about 1 to about 6 carbon atoms;

$R_6$ and $R_7$ are independently selected from the group consisting of allyl, alkyl substituted allyl, and lower alkyl groups having from about 1 to about 6 carbon atoms, and X is oxygen or sulfur wherein at least one of $R_4$ and $R_5$, and at least one of $R_6$ and $R_7$ is an allyl group.

Within the scope of the present invention, certain embodiments are are preferred, namely:

In the thiolcarbamate formula, $R^1$ is ethyl and $R^2$ and $R^3$ each preferably propyl.

In the amine salt, it is preferred that: $R_4$ is ethyl or propyl, $R_5$ is allyl, $R_6$ is ethyl, and $R_7$ is allyl. At least one of $R_4$ and $R_5$ must be an allyl group, and at least one of $R_6$ and $R_7$.

This invention further relates to a method of controlling undesirable vegetation comprising applying the above composition to the locus where control is desired.

The term "alkyl" is used herein in its normal meaning and is intended to include both straight-chain and branched-chain groups.

The term "herbicide", as used herein, means a compound or composition which controls or modifies the growth of plants. By the term "herbicidally effective amount" is meant any amount of such compound or composition which causes a modifying effect upon the growth of plants. By "plants" is meant germinant seeds, emerging seedlings and established vegetation, including roots and above-ground portions. Such controlling or modifying effects include all deviations from natural development, such as killing, retardation, defoliation, desiccation, regulation, stunting, tillering, stimulation, leaf burn, dwarfing and the like.

The phrase "to extend the soil life of said thiolcarbamate" as used herein means to retard the rate at which molecules of thiolcarbamate are broken down into decomposition products when in contact with soil and/or to prolong the period of time following application in which herbicidal effects can be observed. This applies both to field sites where repeated applications of thiolcarbamates have resulted in decreasing herbicidal effectiveness, and to field sites where a decline in activity is detected over time regardless of the prior history of herbicidal applications. An extended soil life can be manifested in a slower rate of decline of weed-killing activity, or an increased half-life of thiolcarbamate concentration in the soil. Other techniques of determining soil life are readily apparent to one skilled in the art.

DETAILED DESCRIPTION OF THE INVENTION

The thiolcarbamates within the scope of the present invention can be prepared by the process described in U.S. Pat. No. 2,913,327 (Tilles et al., Nov. 17, 1959).

The allyl amine salts of the present invention are made by first preparing the thiocarbamic acid in which carbon disulfide, or carbonyl sulfide when X is oxygen, is reacted with an appropriate secondary amine to form the thiocarbamic acid, and this acid is in turn reacted in situ with the appropriate diallyl amine in the presence of an ether solvent to produce the desired salt compound. The method is described more fully in Examples I–III below.

EXAMPLE I

Preparation of N-allyl-N-ethyldithiocarbamic acid N-allyl-N-ethylamine salt

A quantity of 3.57 grams (g) of ethylallyl amine (0.042 mole) plus 1.52 g of carbon disulfide (0.02 mole) was charged into a beaker containing 50 mililiters (ml) of ether. The reaction mixture was allowed to let stand for approximately 15 minutes and the volatiles were then stripped off, leaving behind a residue of 4.9 g of a yellow solid, which was identified by conventional analytical techniques as being the subject compound.

EXAMPLE II

Preparation of N-diallyl thiocarbamic acid N-diallylamine Salt

Ten milliliters (10 ml) of diallylamine (0.81 mole) plus 3 g of carbon disulfide (0.039 mole) were charged into a beaker containing 100 ml of ether. That reation mixture was allowed to let stand for approximately 15 minutes and at the end of that time, the volatiles were stripped off, leaving behind 9.9 g of a yellow solid, which was identified by conventional instrumental techniques as being the subject compounds.

EXAMPLE III

Preparation of N-allyl-N-propyl thiocarbamic acid N-allyl-n-propyl amine salt

A quantity of N-Allyl-n-propylamine (12.7 g of a 35% solution in methanol, 0.042 mole) was dissolved in 50 ml of ethyl ether, plus 1.52 g of carbon disulfide (0.02 mole) was charged into a beaker and the reaction mixture in the beaker was allowed to let stand for approximately 15 minutes, after which time the volatiles were stripped off, leaving behind 3.7 g of a solid residue, which was identified by conventional instrumental techniques as being the subject compound.

Similar procedures can be used to produce the other chemical compounds falling within the purview of the formula described above used as extenders in the present invention.

The objects of the present invention are achieved by applying the allyl amine salt extender compound to the soil at an agricultural field site in conjunction with the thiolcarbamate herbicide. The two compounds can be applied simultaneously in a single mixture or in separate formulations, or they can be applied in succession, where either one following the other. In successive application, it is preferable to add the compounds as close in time as possible.

The herbicide extending effect is operable over a wide range of ratios of the two compounds. It is most convenient, however, to apply the compounds at a ratio of about 0.2:1 to about 20:1 (herbicide/extender) on a weight basis, preferably about 0.5:1 to about 10:1, and most preferably about 0.5:1 to about 5:1.

Thiolcarbamate herbicides useful in the present invention include those disclosed in U.S. Pat. No. 2,913,327, and preferably include S-ethyl N,N-di-n-propylthiolcarbamate, S-ethyl N,N-diisobutylthiolcarbamate, S-n-propyl N,N-di-n-propylthiolcarbamate, and S-n-propyl N-ethyl-N-n-butylthiolcarbamate. Any herbicidally active thiolcarbamate can be used, alone or in admixture with other herbicides, such as triazines.

Specific allyl amine salts which have been found to effective in the compositions of the present invention, include, for example, N-ethyl-N-methallyldithiocarbamic acid-N'-ethyl-N'-methallylamine salt, N-allyl-N-isovaleryldithiocarbamic acid-N-allyl-N-isovalerylamine salt, N-allyl-N-ethyldithiocarbamic acid-N-allyl-N-ethylamine salt, and N-allyl-N-propyldithiocarbamic acid-N-allyl-N-propylamine salt, The variety of crops on which the present composition is useful can be significantly broadened by the use of an antidote to protect the crop from injury and render the composition more selective against weeds.

For antidote descriptions and methods of use, reference is made to U.S. Pat. No. 3,959,304, issued to E. G. Teach on May 25, 1976; U.S. Pat. No. 3,989,503, issued to F. M. Pallos et al. on Nov. 2, 1976; U.S. Pat. No. 4,021,224, issued to F. M. Pallos et al. on May 3, 1977; U.S. Pat. No. 3,131,509 issued to O. L. Hoffman on May 5, 1964; and U.S. Pat. No. 3,564,768, issued to O. L. Hoffman on Feb. 3, 1971.

Examples of useful antidotes include acetamides such as N,N-diallyl-2,2-dichloroacetamide and N,N-diallyl-2-chloroacetamide, oxazolidines such as 2,2,5-trimethyl-N-dichloroacetyl oxazolidine and 2,2-spirocyclohexane-N-dichloroacetyl oxazolidine, and 1,8-naphthalic anhydride. For maximum effect, the antidote is present in the composition in a nonphytotoxic, antidotally effective amount. By "non-phytotoxic" is meant an amount which causes at most minor injury to the crop. By "antidotally effective" is meant an amount which substantially decreases the extent of injury caused by the herbicide to the crop. The preferred weight ratio of herbicide to antidote is about 0.1:1 to about 30:1. The most preferred range for this ratio is about 3:1 to about 20:1.

The following examples are offered to illustrate the utility of the present invention, and are intended neither to limit nor define the invention in any manner.

EXAMPLE IV

Herbicidal Activity Improvement Tests

This example offers herbicidal activity test data to show the effectiveness of the extender compounds in improving the herbicidal activity of thiolcarbamates. The effect is observed by comparing the extent of weed control in test flats treated with a thiolcarbamate against that occurring in similar flats treated with both the thiolcarbamate and the extender. The soil used in this tests was a sandy loam soil from Keeton, Calif., which was pre-treated with the herbicide to simulate a typical field which had received previous herbicide applications.

A. Soil Pre-Treatment

A solution was prepared by diluting an emulsifiable liquid concentrate containing 6 lb/gal (0.72 kg/l) (76.8% by weight) of the herbicide S-ethyl di-n-propyl-thiolcarbamate in 200 ml of water, such that the resulting concentration of herbicide in the solution was 2000 mg/l. Two hundred ml of this solution was then added to 200 lb (90.8 kg) of soil and the mixture was mixed in a rotary mixer for thirty minutes. Also added was 17—17—17 fertilizer (N—$P_2O_5$—$K_2O$ on a weight basis), amounting to 50 ppm by weight with respect to the soil.

The soil was then placed in round plastic containers, 7.5 inches (19.0 cm) in diameter by 7.5 inches (19.0 cm) deep. The soil was tamped and leveled with a row marker to impress three rows across the width of each container. One row was seeded with DeKalb XL-45A corn (*Zea mays*), and two rows were seeded with barnyardgrass (*Echinochloa crusgalli*). Sufficient seeds were planted to produce several seedlings per row. The containers were then placed in a greenhouse maintained at 20° C. to 30° C. and watered daily by sprinkler.

Five weeks after treatment, the soil was allowed to dry out and the plant foliage was removed. The soil was then passed through a 0.25 inch (0.64 cm) screen to remove plant roots and clods, and then passed through a 2 millimeter (mm) screen.

B. Herbicide Test

The same thiolcarbamate preparation described in Part A was used. The extender compounds were used in technical form. These materials were added to 100 cc mixtures of equal parts of water and acetone at such amounts that 5 cc of the resulting mixture when added to three pounds of soil yielded a quantity in the soil equivalent to the desired application rate expressed in pounds per acre. Thus, 5 cc of the mixture and three pounds of soil were placed in a rotary mixer.

The treated soil was then placed in aluminum flats which were 3 inches deep, 4 inches wide, and 8 inches long (7.6×10.2×20.3 cm). The soil was tamped and leveled with a row marker to impress six rows across the width of the flat. The test weeds were as follows:

| COMMON NAME | SCIENTIFIC NAME |
|---|---|
| watergrass | *Echinochloa crusgalli* (L.) |
| milo | *Sorghum bicolor* (L.) Moench |
| wild oats | *Avena fatua* (L.) |
| wild cane | *Sorghum bicolor* (L.) Moench |
| yellow foxtail | *Setaria lutescens* (Weigle) Hubb. |

DeKalb XL-45A corn of species *Zea mays* (L.) was also planted.

Sufficient seeds were planted to produce several seedlings per inch in each row. The flats were then placed in a greenhouse maintained at 70° to 85° F. (21° to 30° C.) and watered daily by sprinkler.

Approximately three weeks after treatment, the degree of weed control and corn injury were estimated and recorded as percentage control compared to the growth of the same species in an untreated check flat of the same age. The rating scale ranges from 0 to 100%, where 0 equals no effect with plant growth equal to the untreated control, and 100 equals complete kill.

The results are listed in Table I. Control experiments (with no extender present) are included in each batch for comparison. Substantial improvements in average percent weed control over the control experiments are evident. The herbicidal efficacy of the thiolcarbamate three weeks after application was much improved by the use of the extender, whereas the corn remained unaffected.

TABLE I

| HERBICIDE TEST RESULTS | | | |
|---|---|---|---|
| Additive | Application Rate (lb/A) | Average % Weed Control | % Corn Injury |
| NONE (Control) | 3 | 9 | 0 |
| N—allyl-N—ethyldithiocarbamic acid-N—allyl-N—ethylamine salt | 4 | 90 | 70 |
| N—allyl-N—propyldithiocarbamic acid-N—allyl-N—propylamine salt | 4 | 18 | 0 |
| N—allyl-N—isovaleryldithiocarbamic acid-N—allyl-N—isovalerylamine salt | 4 | 22 | 0 |
| N—allyl-N—butyldithiocarbamic acid-N'—allyl-N'—butylamine salt | 4 | 26 | 0 |
| N—allyl-N—amyldithiocarbamic acid-N'—allyl-N'—allylamine salt | 4 | 31 | 0 |
| N—allyl-N—methyldithiocarbamic acid-N'—allyl-N'—methylamine salt | 4 | 58 | 0 |
| N—ethyl-N—methallyldithiocarbamic acid-N'—ethyl-N'—methallylamine salt | 4 | 22 | 0 |
| S—methyl-N,N—diallyl thiocarbamate | 4 | 24 | 0 |
| N,N—diallyldithiocarbamic acid diallylamine salt | 4 | 91 | 0 |

HERBICIDE: S—Ethyl N,N—di-n-propylthiolcarbamate (EPTC) at 3 lb/A
EXTENDER: As shown, at application rate shown
EVALUATION TIME: 3 Weeks after treatment

EXAMPLE V

This example shows, by soil analysis, the effectiveness of the extender compounds of the present invention in extending the soil life of thiolcarbamates. The thiolcarbamate preparation described in Example IV was used, and the soil was a silty loam from Mississippi.

A. Soil Pre-Treatment

As in Example 2, the soil was pre-treated with the herbicide to simulate a typical field with a history of herbicide treatment. The procedure was identical to that described in part A of Example IV.

B. Soil Persistence Test

A 100-gram quantity (air-dry basis) of the pre-treated soil was placed in an 8-ounce (0.25 liter) wide-mouth glass bottle. The emulsifiable concentrate described in Part A above was appropriately diluted in water such that a 5-ml portion added to the soil would produce a herbicide concentration of 6 ppm (weight) in the soil. This is equivalent to an application rate of 6 pounds per acre (6.7 kilograms per hectare) in a field where the herbicide is incorporated into the soil through a depth of about 2 inches (5.08 cm) soon after application. A selected extender compound in technical (nonformulated) form was then diluted in an acetone-water mixture such that a one-ml portion added to the soil would produce a concentration of 4 ppm by weight, equivalent to 4 pouds per acre (4.5 kilograms per hectare). On these bases, the herbicide and extender were added to the bottle containing the soil.

Following such treatment, the soil was moistened with 20 ml of deionized water. The bottle was then covered with a watch glass to maintain aerobic conditions and to prevent rapid soil drying, and placed in a controlled environmental chamber in darkness, where the temperature was maintained constant at 25° C.

Four days later, the bottle was removed from the environmental chamber and 25 ml of water and 100 ml of toluene were added. The bottle was then tightly sealed with a lid containing four-layer cellophane liners, and vigorously shaken on a variable speed, reciprocating shaker (Eberbach Corp. Model 6000) set at approximately 150 excursions per minute for ninety minutes. After shaking, the bottle contents were allowed to settle, and a 10 ml aliquot of toluene was transferred by pipette into a glass vial and sealed with a polyseal cap. The toluene extract was analyzed for herbicidal content by gas chromatography. The chromatograph data was then converted to equivalent soil concentrations in parts per million (ppm) by weight of the herbicide.

The results are shown in the table below, where a variety of compounds were tested in two separately treated batchs of soil. A control run without an extender compound was conducted for each soil batch, to show how the drop in herbicide concentration was affected by the extender compound. In each case, the quantity of herbicide remaining in the soil after four days was dramatically increased when the extender compound was added.

TABLE II

4-DAY SOIL PERSISTENCE DATA

| Additive | EPTC Residue After 4 days (ppm) | |
|---|---|---|
| | With Extender | Without Extender |
| N—allyl-N—ethyldithiocarbamic acid-N—allyl-N—ethylamine salt | 2.54 | 0.05 |
| N—allyl-N—propyldithiocarbamic acid-N—allyl-N—propylamine salt | 1.05 | 0.00 |
| N—allyl-N—isovaleryldithiocarbamic acid-N—allyl-N—isovalerylamine salt | 1.03 | 0.00 |
| N—allyl-N—butyldithiocarbamic acid-N'—allyl-N'—butylamine salt | 1.00 | 0.00 |
| N—allyl-N—amyldithiocarbamic acid-N'—allyl-N'—allylamine salt | 0.90 | 0.00 |
| N—allyl-N—methyldithiocarbamic acid-N'—allyl-N'—methylamine salt | 0.25 | 0.00 |
| N—ethyl-N—methallyldithiocarbamic acid-N'—ethyl-N'—methallylamine salt | 1.39 | 0.00 |
| S—methyl-N,N—diallyl thiocarbamate | 1.40 | 0.00 |
| N,N—diallyldithiocarbamic acid diallylamine salt | 2.34 | 0.05 |

Herbicide: S—Ethyl N,N—di-n-propylthiolcarbamate (EPTC) at 6 ppm (6 lb/A)
Extender: As shown at 4 ppm (4 lb/A)

As seen from the tables above, the quantity of herbicide remaining in the soil was dramatically increased when the extender compound was added. Similar results can be achieved using the other extender compounds falling within the scope of the formula as claimed.

METHODS OF APPLICATION

The herbicidal compositions of the present invention are useful in controlling the growth of undesirable vegetation by pre-emergence or post-emergence application to the locus where control is desired, including pre-plant and post-plant soil incorporation as well as surface application. The compositions are generally embodied in formulations suitable for convenient application. Typical formulations contain additional ingredients or diluent carriers which are either inert or active. Examples of such ingredients or carriers are water, organic solvents, dust carriers, granular carriers, surface active agents, oil and water, water-oil emulsions, wetting agents, dispersing agents, and emulsifying agents. The herbicidal formulations generally take the form of dusts, emulsifiable concentrates, granules and pellets, or microcapsules.

A. Dusts

Dusts are dense powder compositions which are intended for application in dry form. Dusts are characterized by their free-flowing and rapid settling properties so that they are not readily windborne to areas where their presence is not desired. They contain primarily an active material and a dense, free-flowing, solid carrier.

Their performance is sometimes aided by the inclusion of a wetting agent, and convenience in manufacture frequently demands the inclusion of an inert, absorptive grinding aid. For the dust compositions of this invention, the inert carrier may be either of vegetable or mineral origin, the wetting agent is preferably anionic or nonionic, and suitable absorptive grinding aids are of mineral origin.

Suitable classes of inert solid carriers for use in the dust compositions are those organic or inorganic powders which possess high bulk density and are very free-flowing. They are also characterized by low surface area and poor liquid absorptivity. Suitable grinding aids are natural clays, diatomaceous earths, and synthetic mineral fillers derived from silica or silicate. Among ionic and nonionic wetting agents, the most suitable are the members of the group known to the art as wetting agents and emulsifiers. Although solid agents are preferred because of ease of incorporation, some liquid nonionic agents are also suitable in the dust formulations.

Preferred dust carriers are micaceous talcs, pyrophyllite, dense kaolin clays, tobacco dust and ground calcium phosphate rock. Preferred grinding aids are attapulgite clay, diatomaceous silica, synthetic fine silica and synthetic calcium and magnesium silicates.

Most preferred wetting agents are alkylbenzene and alkyl-naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Preferred dispersants are methyl cellulose, polyvinyl alcohol, lignin sulfonates, polymeric alkylnaphthalene sulfonates, sodium naphthalenesulfonate, polymethylene bisnaphthalenesulfonate, and sodium-N-methyl-N-(long chain acid) taurates.

The inert solid carriers in the dusts of this invention are usually present in concentrations of from about 30 to 90 weight percent of the total composition. The grinding aid will usually constitute 5 to 50 weight percent of the compositions, and the wetting agent will constitute from about 0 to 1.0 weight percent of the composition. Dust compositions can also contain other surfactants such as dispersing agents in concentrations of up to about 0.5 weight percent, and minor amounts of anticaking and antistatic agents. The particle size of the carrier is usually in the range of 30 to 50 microns.

B. Emulsifiable Concentrates

Emulsifiable concentrates are usually solutions of the active materials in nonwater-miscible solvents together with an emulsifying agent. Prior to use, the concentrate is diluted with water to form a suspended emulsion of solvent droplets.

Typical solvents for use in emulsifiable concentrates include weed oils, chlorinated hydrocarbons, and nonwater-miscible ethers, esters, and ketones.

Typical emulsifying agents are anionic or nonionic surfactants, or mixtures of the two. Examples include long-chain alkyl or mercaptan polyethoxy alcohols, alkylaryl polyethoxy alcohols, sorbitan fatty acid esters, polyoxyethylene ethers with sorbitan fatty acid esters, polyoxyethylene glycol esters with fatty or rosin acids, fatty alkylol amide condensates, calcium and amine salts of fatty alcohol sulfates, oil soluble petroleum sulfonates, or preferably mixtures of these emulsifying agents. Such emulsifying agents will comprise from about 1 to 10 weight percent of the total composition.

Thus, emulsifiable concentrates of the present invention will consist of from about 15 to about 50 weight percent active material, about 40 to 82 weight percent solvent, and about 1 to 10 weight percent emulsifier. Other additives such as spreading agents and stickers can also be included.

C. Granules and Pellets

Granules and pellets are physically stable, particulate compositions containing the active ingredients adhering to or distributed through a basic matrix of a coherent, inert carrier with macroscopic dimensions. A typical particle is about 1 to 2 millimeters in diameter. Surfactants are often present to aid in leaching of the active ingredient from the granule or pellet.

The carrier is preferably of mineral origin, and generally falls within one of two types. The first are porous, absorptive, preformed granules, such as preformed and screened granular attapulgite or heat expanded, granular, screened vermiculite. On either of these, a solution of the active agent can be sprayed and will be absorbed at concentrations up to 25 weight percent of the total weight. The second, which are also suitable for pellets, are initially powdered kaolin clays, hydrated attapulgite, or bentonite clays in the form of sodium, calcium, or magnesium bentonites. Water-soluble salts, such as sodium salts, may also be present to aid in the disintegration of granules or pellets in the presence of moisture. These ingredients are blended with the active components to give mixtures that are granulated or pelleted, followed by drying, to yield formulations with the active component distributed uniformly throughout the mass. Such granules and pellets can also be made with 25 to 30 weight percent active component, but more frequently a concentration of about 10 weight percent is desired for optimum distribution. The granular compositions of this invention are most useful in a size range of 15-30 mesh.

The surfactant is generally a common wetting agent of anionic or nonionic character. The most suitable wetting agents depend upon the type of granule used. When preformed granules are sprayed with active material in liquid form the most suitable wetting agents are nonionic, liquid wetters miscible with the solvent. These are compounds most generally known in the art as emulsifiers, and comprise alkylaryl polyether alcohols, alkyl polyether alcohols, polyoxyethylene sorbitan fatty acid esters, polyethylene glycol esters with fatty or rosin acids, fatty alkylol amide condensates, oil solution petroleum or vegetable oil sulfonates, or mixtures of these. Such agents will usually comprise up to about 5 weight percent of the total composition.

When the active ingredient is first mixed with a powdered carrier and subsequently granulated, or pelleted, liquid nonionic wetters can still be used, but it is usually preferable to incorporate at the mixing stage one of the solid, powdered anionic wetting agents such as those previously listed for the wettable powders. Such agents will comprise from about 0 to 2 weight percent of the total composition.

Thus, the preferred granular or pelleted formulations of this invention comprise about 5 to 30 percent by weight active material, about 0 to 5 weight percent wetting agent, and about 65 to 95 weight percent inert material carrier, as these terms are used herein.

D. Microcapsules

Microcapsules consist of fully enclosed droplets or granules containing the active materials, in which the enclosing material is an inert porous membrane, arranged to allow escape of the enclosed materials to the surrounding medium at controlled rates over a specified period. Encapsulated droplets are typically about 1 to 50 microns in diameter.

The enclosed liquid typically constitutes about 50 to 95% of the weight of the entire capsule, and may contain a small amount of solvent in addition to the active materials.

Encapsulated granules are characterized by porous membranes sealing the openings of the granule carrier pores, trapping the liquid containing the active components inside for controlling release. A typical granule size ranges from 1 millimeter to 1 centimeter in diameter. In agricultural usage, the granule size is generally about 1 to 2 millimeters in diameter. Granules formed by extrusion, agglomeration, or prilling are useful in the present invention as well as materials in their naturally occurring form. Examples of such carriers are vermiculite, sintered clay granules, kaolin, attapulgite clay, sawdust, and granular carbon.

Useful encapsulating materials include natural and synthetic rubbers, cellulosic materials, styrene-butadiene copolymers, polyacrylonitriles, polyacrylates, polyesters, polyamides, polyurethanes, and starch xanthates.

E. In General

Each of the above formulations can be prepared as a package containing both the herbicide and the extender together with the other ingredients of the formulation (diluents, emulsifiers, surfactants, etc.). The formulations can also be prepared by a tank mix method, in which the ingredients are obtained separately and combined at the grower site. The herbicide and extender may both be used in the same type of formulation or a different formulation may be used for each, e.g. the herbicide may be in microcapsule form while the extender may be an emulsifiable concentrate, or vice versa.

As a further alternative, the herbicide and extender can be applied sequentially, with either being applied first. This is a less preferred method, however, since more effective results are obtained with simultaneous application.

In general, any conventional method of application can be used. The locus of application can be soil, seeds, seedlings, or the actual plants, as well as flooded fields. Soil application is preferred. Dusts and liquid compositions can be applied by the use of powder dusters, boom and hand sprayers, and spray dusters. The compositions can also be applied from airplanes as dusts and sprays because they are effective in very low dosages. In order to modify or control the growth of germinating seeds or emerging seedlings, as a typical example, the dust and liquid compositions are applied to the soil according to conventional methods and are distributed in the soil to a depth of at least one-half inch below the soil surface. It is not necessary that the phytotoxic compositions be admixed with the soil particles. Instead, the compositions can be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The herbicide/extender compositions can also be applied to the soil through irrigation systems. According to this technique, the compositions are added directly to irrigation water immediately prior to irrigation of the field. This technique is applicable in all geographical areas regardless of rainfall, since it permits supplementation of the natural rainfall at critical stages of plant growth. In a typical application, the concentration of the herbicide/extender composition in the irrigation water will range from about 10 to 150 parts per million by weight. The irrigation water can be applied by the use of sprinkler systems, surface furrows, or flooding. Such application is most effectively done before the weeds germinate, either early in the spring prior to germination or within two days after cultivation of the field.

The amount of the present composition which constitutes a herbicidally effective amount depends upon the nature of the seeds of plants to be controlled. The rate of application of active ingredient varies from about 0.01 to about 50 pounds per acre, preferably about 0.1 to about 25 pounds per acre with the actual amount depending on the overall cost and the desired results. It will be readily apparent to one skilled in the art that compositions exhibiting lower herbicidal activity will require a higher dosage than more active compounds for the same degree of control.

What is claimed:
1. An herbicidal composition consisting essentially of
   (a) an herbicidally effective amount of a thiolcarbamate having the formula

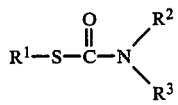

in which $R^1$, $R^2$, and $R^3$ are independently $C_1$–$C_6$ alkyl; and
   (b) an amount of an allyl amine salt of thiocarbamic acid compound sufficient to extend the soil life of said thiolcarbamate, said allyl amine salt compound having the formula

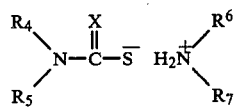

wherein
   $R_4$ and $R_5$ are independently selected from the group consisting of allyl, and lower alkyl groups having from about 1 to about 6 carbon atoms;
   $R_6$ and $R_7$ are independently selected from the group consisting of allyl, and lower alkyl groups having from about 1 to about 6 carbon atoms, and
   X is sulfur wherein at least one of $R_4$ and $R_5$, and at least one of $R_6$ and $R_7$ is an allyl group, and wherein the ratio of (a) to (b) ranges from about 3:4 to about 6:4 by weight.

2. An herbicidal composition consisting essentially of (a) an herbicidally effective amount of S-ethyl N,N-di-n-propylthiolcarbamate and (b) an amount of an allyl amine salt of thiocarbamic acid compound sufficient to extend the soil life of said thiolcarbamate, said salt compound having the formula

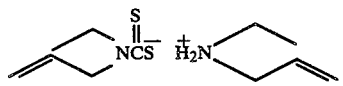

wherein the ratio of (a) to (b) ranges from about 3:4 to about 6:4 by weight.

3. An herbicidal composition consisting essentially of (a) an herbicidally effective amount of S-ethyl N,N-di-n-propylthiolcarbmate and (b) an amount of an allyl amine salt of thiocarbamic acid compound sufficient to extend the soil life of said thiolcarbamate, said salt compound having the formula

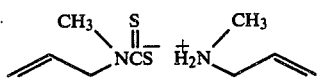

wherein the ratio of (a) to (b) ranges from about 3:4 to about 6:4 by weight.

4. A method of controlling undesirable vegetation consisting essentially of applying to the locus where control is desired both
   (a) an herbicidally effective amount of a thiolcarbamate of the formula

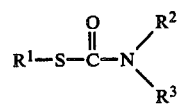

in which $R^1$, $R^2$, and $R^3$ are independently $C_1$–$C_6$ alkyl; and
   (b) an amount of an allyl amine salt of thiocarbamic acid compound sufficient to extend the soil life of said thiolcarbamate, said salt compound having the formula

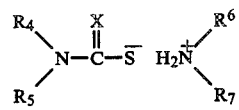

wherein
   $R_4$ and $R_5$ are independently selected from the group consisting of allyl, and lower alkyl groups having from about 1 to about 6 carbon atoms;
   $R_6$ and $R_7$ are independently selected from the group consisting of allyl, and lower alkyl groups having from about 1 to about 6 carbon atoms; and
   X is sulfur wherein at least one of $R_4$ and $R_5$ and at least one of $R_6$ and $R_7$ is an allyl group, and wherein the ratio of (a) to (b) ranges from about 3:4 to about 6:4 by weight.

5. A method of controlling undesirable vegetation consisting essentially of (a) applying to the locus where control is desired an herbicidally effective amount of S-ethyl N,N-di-n-propylthiolcarbamate and (b) an amount of an allyl amine salt of thiocarbamic acid compound sufficient to extend the soil life of said thiolcarbamate, said salt compound having the formula

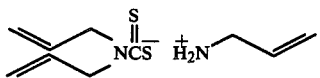

wherein the ratio of (a) to (b) ranges from about 3:4 to about 6:4 by weight.

6. A method of controlling undesirable vegetation consisting essentially of (a) applying to the locus where control is desired an herbicidal composition comprising an herbicidally effective amount of S-ethyl N,N-di-n-propylthiolcarbamate and (b) an amount of an allyl amine thiocarbamic acid of thiocarbamic acid compound sufficient to extend the soil life of said thiolcarbamate, said salt compound having the formula

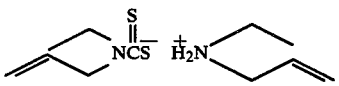

wherein the ratio of (a) to (b) ranges from about 3:4 to about 6:4 by weight.

7. A method of extending the soil life of a thiolcarbamate having the formula

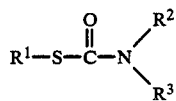

in which $R^1$, $R^2$ and $R^3$ are independently $C_1$–$C_6$ alkyl; which consists essentially of applying to the soil containing said thiolcarbamate or to which said thiolcarbamate is to be applied an effective amount of an allyl amine salt of thiocarbamic acid compound having the formula

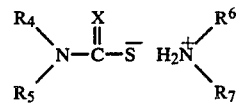

wherein
- $R_4$ and $R_5$ are independently selected from the group consisting of allyl, and lower alkyl groups having from about 1 to about 6 carbon atoms;
- $R_6$ and $R_7$ are independently selected from the group consisting of allyl, and lower alkyl groups having from about 1 to about 6 carbon atoms; and
- X is sulfur wherein at least one of $R_4$ and $R_5$ and at least one of $R_6$ and $R_7$ is an allyl group, and wherein the ratio of (a) to (b) ranges from about 3:4 to about 6:4 by weight.

8. A method of extending the soil life of S-ethyl N,N-di-n-propylthiolcarbamate which consists essentially of applying to the soil containing said thiolcarbamate or to which said thiolcarbamate is to be applied an effective amount of an allyl amine salt of thiocarbamic acid compound having the formula

wherein the ratio of said thiolcarbamate to said allylamine salt ranges from about 3:4 to about 6:4 by weight.

9. A method of extending the soil life of S-ethyl N,N-di-npropylthiolcarbamate which consists essentially of applying to the soil containing said thiolcarbamate or to which said thiolcarbamate is to be applied an effective amount of an allyl amine salt of thiocarbamic acid compound having the formula

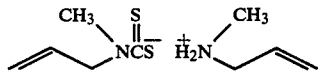

wherein the ratio of said thiolcarbamate to said allylamine slat ranges from about 3:4 to about 6:4 by weight.

* * * * *